(12) United States Patent
Janka et al.

(10) Patent No.: US 9,006,470 B2
(45) Date of Patent: *Apr. 14, 2015

(54) METHOD OF SYNTHESIZING LOW COLOR FURAN DIESTERS

(71) Applicant: Eastman Chemical Company, Kingsport, TN (US)

(72) Inventors: Mesfin Ejerssa Janka, Kingsport, TN (US); John Dayton Baker, Jr., Kingsport, TN (US); Stephanie Nicole Rollins, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,941

(22) Filed: Nov. 8, 2012

(65) Prior Publication Data

US 2014/0128623 A1 May 8, 2014

(51) Int. Cl.
| | | |
|---|---|---|
| *C07D 307/62* | (2006.01) | |
| *C07D 307/68* | (2006.01) | |
| *C07D 307/24* | (2006.01) | |
| *C07D 307/18* | (2006.01) | |

(52) U.S. Cl.
CPC ............ *C07D 307/68* (2013.01); *C07D 307/24* (2013.01); *C07D 307/18* (2013.01)

(58) Field of Classification Search
CPC .... C07D 307/24; C07D 307/18; C07G 45/15; C07G 45/10; C07G 45/06
USPC .......................................... 549/485; 208/264
See application file for complete search history.

(56) References Cited

U.S. PATENT DOCUMENTS

| | | | |
|---|---|---|---|
| 2,819,289 A * | 1/1958 | Lüben ............................. 208/27 |
| 3,225,066 A | 12/1965 | Lew | |
| 3,259,636 A | 7/1966 | Lew | |
| 3,546,255 A | 12/1970 | Duennenberger et al. | |
| 3,994,931 A * | 11/1976 | Johnson et al. ............... 549/505 |
| 7,385,081 B1 * | 6/2008 | Gong ............................. 562/405 |
| 8,796,477 B2 * | 8/2014 | Janka et al. ................... 549/485 |
| 2011/0263916 A1 * | 10/2011 | Bao et al. ....................... 585/254 |

FOREIGN PATENT DOCUMENTS

| | | |
|---|---|---|
| EP | 2 481 773 A1 | 8/2012 |
| GB | 819438 A | 9/1959 |
| WO | WO 2011/023491 A1 | 3/2011 |
| WO | WO 2012/017052 A1 | 2/2012 |
| WO | WO 2012/002681 A1 | 3/2012 |
| WO | WO 2012/161970 A2 | 11/2012 |

OTHER PUBLICATIONS

Sanderson, R. D., et al.; Synthesis and Evaluation of Dialkyl Furan-2,5-Dicarboxylates as Plasticizers for PVC, Journal of Applied Polymer Science, vol. 53, (1994), pp. 1785-1793.
Copending U.S. Appl. No. 13/672,022, filed Nov. 8, 2012, Mesfin Ejerssa Janka.
Notification of Transmittal of the International Search Report and the Written Opinion of the International Searching Authority, or the Declaration; International Application No. PCT/US2013/068423; Mailing Date: Apr. 7, 2014.
USPTO Office Action dated Oct. 3, 2013 in co-pending U.S. Appl. No. 13/672,022.
Notification of Transmittal of the International Search Report and the Written Opinion of the International Searching Authority, or the Declaration; International Application No. PCT/US2013/068419; Mailing Date: Dec. 12, 2013.
Lewkowski, J; Convenient Synthesis of Furan-2,5-dicarboxylic Acid and its Derivatives; Polish Journal of Chemistry, vol. 75, pp. 1943-1946 (2001).
USPTO Office Action dated Sep. 5, 2014 in co-pending U.S. Appl. No. 13/672,022.

* cited by examiner

*Primary Examiner* — Andrew D Kosar
*Assistant Examiner* — Raymond Covington
(74) *Attorney, Agent, or Firm* — Dennis V. Carmen

(57) ABSTRACT

The present invention relates to a method of synthesizing a low colored furan-2,5-dicarboxylate derivative plasticizer by utilizing purified FDCA (pFDCA), which has very low level 5-formyl furan-2-carboxyic acid (FFCA) and very low level colored bodies, and an alcohol.

20 Claims, No Drawings

METHOD OF SYNTHESIZING LOW COLOR FURAN DIESTERS

BACKGROUND

Plasticizers have the ability to reduce the glass transition temperature of polymers and thereby provide soft and/or flexible products. Plasticizers are often based on esters of polycarboxylic acids with linear or branched aliphatic alcohols of moderate chain length. Organic ester phthalates are widely used plasticizers. The most commonly used phthalate esters are di-2-ethylhexyl phthalate (DEHP), also known as dioctyl phthalate (DOP), diisononyl phthalate (DINP) and diisodecyl phthalate (DIDP). These aromatic dicarboxylic plasticizers are commonly synthesized from terephthalic acid or dimethyl terephthalate and the corresponding alcohol. There is a growing interest in the use of renewable resources as feed stocks for the chemical industries mainly due to the progressive reduction of fossil reserves and their related environmental impacts.

Furan-2,5-dicarboxylic acid (FDCA) is a versatile intermediate considered as a promising closest biobased alternative to terephthalic acid. Like aromatic diacids, FDCA undergoes esterification reaction with an alcohol such as 2-ethylhexanol to form bis(2-ethylhexyl)furan-2,5-dicarboxylate (BEHFD) plasticizer. BEHFD plasticizer can synthesized from FDCA and 2-ethylhexan-1-ol (2-EH), in the presence of a catalyst as shown below in equation (1), or by transesterification of dimethyl furan-2,5-dicarboxylate (DMFD) with 2-EH in the presence of a catalyst as shown below in equation (2).

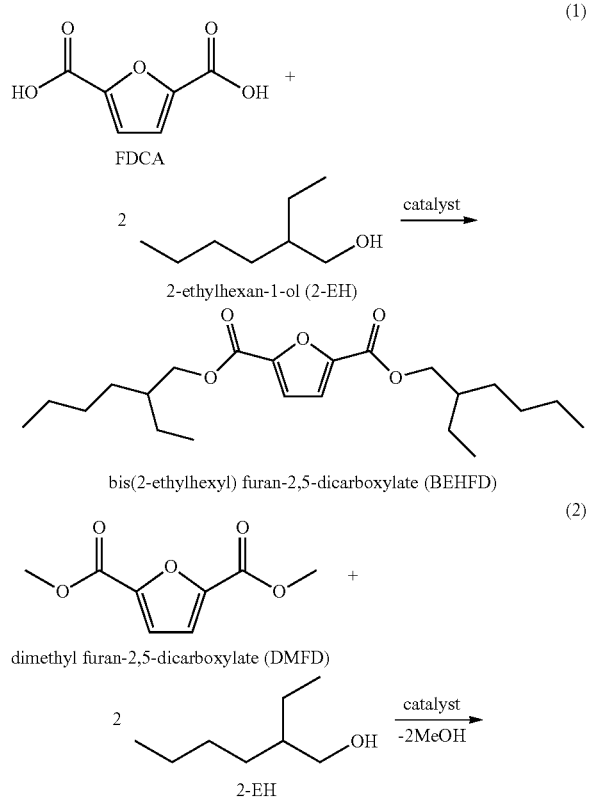

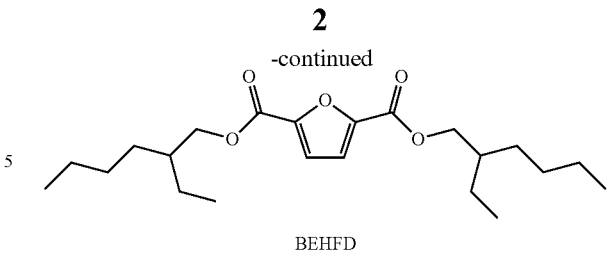

BEHFD

However, the above synthetic pathways to make BEHFD yield very highly colored plasticizer which makes its end use application less desirable.

SUMMARY

This summary is provided to introduce simplified concepts of producing low color furan based diesters. Additional details of example methods are further described below in the Detailed Description. This summary is not intended to identify essential features of the claimed subject matter, nor is it intended for use solely in determining the scope of the claimed subject matter.

According to a first embodiment, the present invention concerns a method for preparing a furan-2,5-dicarboxylate derivative plasticizer, comprising:
 a) providing a purified furan-2,5-dicarboxylic acid composition; and
 b) contacting said purified furan-2,5-dicarboxylic acid composition and an alcohol stream in the presence of a catalyst to produce a low color furan-2,5-dicarboxylate derivative plasticizer.

Another embodiment concerns a method for preparing a furan-2,5-dicarboxylate derivative plasticizer, comprising:
 a) providing a crude furan 2,5-dicarboxylic acid composition comprising furan 2,5-dicarboxylic acid solids, 5-formyl furan-2-carboxyic acid, and a oxidation solvent composition;
 b) combining a hydrogenation solvent composition with the furan 2,5-dicarboxylic acid solids and dissolving at least a portion of the furan 2,5-dicarboxylic acid solids to thereby produce a solvated furan 2,5-dicarboxylic acid composition comprising dissolved furan 2,5-dicarboxylic acid, the hydrogenation solvent composition, and 5-formyl furan-2-carboxyic acid;
 c) in a hydrogenation reaction zone, hydrogenating the solvated furan 2,5-dicarboxylic acid at a temperature within a range of 130° C. to 225° C. by contacting the solvated furan 2,5-dicarboxylic acid composition with hydrogen in the presence of a hydrogenation catalyst to thereby hydrogenate 5-formyl furan-2-carboxyic acid and produce a hydrogenated furan 2,5-dicarboxylic acid composition comprising a hydrogenated 5-formyl furan-2-carboxyic acid species, dissolved furan 2,5-dicarboxylic acid, and the hydrogenation solvent; and
 d) separating at least a portion of the dissolved FDCA from the hydrogenated furan 2,5-dicarboxylic acid composition to obtain a purified furan 2,5-dicarboxylic acid composition; and
 e) contacting said purified furan 2,5-dicarboxylic acid composition and an alcohol stream in the presence of a catalyst to produce a low color furan-2,5-dicarboxylate derivative plasticizer.

Still another embodiment concerns a method for preparing a furan-2,5-dicarboxylate derivative plasticizer, comprising:
 a) oxidizing in an primary oxidation zone a composition including 5-(hydroxymethyl)furfural; 5-(hydroxymethyl)furfural esters; 5-(hydroxymethyl)furfural ethers; 5-alkyl furfurals; mixed feedstocks of 5-(hydroxymethyl)furfural and 5-(hydroxymethyl)furfural esters, mixed feedstocks of 5-(hydroxymethyl)furfural and 5-(hydroxymethyl)furfural ethers, mixed feedstocks of 5-(hydroxymethyl)furfural and 5-alkyl furfurals or mixtures thereof in the presence of a solvent stream, an oxidizing gas stream, and a catalyst system to produce a carboxylic acid composition comprising 2,5-dicarboxylic acid composition;

b) routing the carboxylic acid composition to a liquid displacement zone to produce a displaced mother liquid stream and a low impurity slurry stream; and c) routing the low impurity slurry stream to a secondary oxidation zone to form a purified slurry stream, wherein the purified slurry stream comprises purified 2,5-dicarboxylic acid composition and wherein the oxidizing temperature in the secondary oxidation zone is at least 10° C. higher that the oxidizing temperature in the primary oxidation zone; and d) contacting said purified 2,5-dicarboxylic acid composition and an alcohol stream in the presence of a catalyst to produce a low color furan-2,5-dicarboxylate derivative plasticizer.

DETAILED DESCRIPTION

According to an embodiment, the present invention concerns a method for preparing a low colored furan-2,5-dicarboxylate derivative plasticizer, such as BEHFD, by utilizing purified FDCA (pFDCA) which has low level 5-formyl furan-2-carboxyic acid (FFCA) and low level color bodies. As used herein, "low color furan-2,5-dicarboxylate derivative" means a furan-2,5-dicarboxylate derivative having an APHA color of less than 100; less than 60 less than 40; or less than 20. Alternatively, "low color furan-2,5-dicarboxylate derivative" means a furan-2,5-dicarboxylate derivative having a b* value of less than 10; less than 5.0 less than 2.0; or less than 1.0.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

All amounts are by weight unless otherwise specified. All amounts by weight are based on the weight of the whole composition stream containing the ingredient in question rather than a part of that composition or a different stream altogether, unless otherwise noted. All stated amounts in ppm are by weight (ppmw) unless otherwise noted.

According to an embodiment, the present disclosure concerns the use of purified FDCA for obtaining a low colored furan-2,5-dicarboxylate derivative plasticizers, such as BEHFD. Moreover, the low colored furan-2,5-dicarboxylate derivative plasticizers obtained by the methods described herein show good fusion, lower volatility and better efficiency than DEHP for PVC application. According to an embodiment, the purified FDCA can be obtained from crude FDCA via, for example, post oxidation and solvent displacement or by hydrogenation processes.

By way of example, a post oxidation and solvent displacement process can be accomplished via oxidizing in a primary oxidation zone a composition including 5-(hydroxymethyl) furfural (5-HMF), 5-HMF esters (5-R(CO)OCH2-furfural where R=alkyl, cycloalkyl and aryl), 5-HMF ethers (5-R'OCH2-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, mixed feedstocks of 5-HMF and 5-alkyl furfurals or mixtures thereof in the presence of a solvent stream, an oxidizing gas stream, and a catalyst system to produce a carboxylic acid composition comprising (FDCA). The method further includes routing the carboxylic acid composition to a liquid displacement zone to produce a displaced mother liquid stream and a low impurity slurry stream and then routing the low impurity slurry stream to a secondary oxidation zone to form a purified slurry stream. The purified slurry stream comprises purified FDCA. Moreover, the oxidizing temperature in the secondary oxidation zone is at least 10° C. higher that the oxidizing temperature in the primary oxidation zone.

According to another embodiment, purified FDCA can be obtained from crude FDCA via, for example, hydrogenation processes. By way of example, hydrogenating crude FDCA to form purified FDCA can be accomplished via a) providing a crude FDCA composition comprising furan 2,5-dicarboxylic acid (FDCA) solids, 5-formyl furan-2-carboxyic acid (FFCA), and a oxidation solvent composition; b) combining a hydrogenation solvent composition with the FDCA solids and dissolving at least a portion of the FDCA solids to thereby produce a solvated FDCA (sFDCA) composition comprising dissolved FDCA, the hydrogenation solvent composition, and FFCA; and c) in a hydrogenation reaction zone, hydrogenating the sFDCA at a temperature within a range of 130° C. to 225° C. by contacting the sFDCA composition with hydrogen in the presence of a hydrogenation catalyst to thereby hydrogenate FFCA and produce a hydrogenated furan 2,5-dicarboxylic acid composition (hFDCA) comprising a hydrogenated FFCA species, dissolved FDCA, and the hydrogenation solvent; and d) separating at least a portion of the dissolved FDCA from the hFDCA composition to obtain a purified 5-formyl furan-2-carboxyic acid level of less than 200 ppm, less than 100, less than 50, less than 30, less than 20 or less than 10 and/or a B* value of less than 10; less than 5.0 less than 2.0; or less than 1.0.

According an embodiment, the present description concerns a method for producing a furan-2,5-dicarboxylate derivative, such as BEHFD, which includes contacting a purified furan diester, such as furan-2,5-dicarboxylic acid, composition and an alcohol stream in the presence of a catalyst under esterification conditions to produce a furan-2,5-dicarboxylate derivative, wherein the furan-2,5-dicarboxylate derivative has an APHA color of less than 100, less than 60, less than 40, or less than 20 and/or a B* value of less than 10; less than 5.0 less than 2.0; or less than 1.0.

Alcohols useful in the alcohol stream can include, but are not limited to, iso-, normal, unbranched, branched, linear, cyclo and/or aryl isomers of $C_4$ to $C_{13}$ alcohols or mixtures thereof. Examples of such alcohols include butanol, pentanol, hexanol, heptanol, octanol (including 2-ethylhexanol), nonanol, decanol, undecanol, dodecanol, 2-phenyl ethanol, cyclohexanol, cyclohexanemethanol, methylcyclo-hexanemethanol, 1,4-cyclohexanedimethanol, benzyl alcohol and mixtures thereof. According to an embodiment, the alcohol stream can include a mixture of two or more alcohols.

Moreover, examples of the type of furan diesters that can be produced include, but are not limited to, dibutyl furan-2,5-dicarboxylate, dipentyl furan-2,5-dicarboxylate, dihexyl furan-2,5-dicarboxylate, di-heptyl furan-2,5-dicarboxylate, bis(2-ethylhexyl)furan-2,5-dicarboxylate, bis(dioctyl)furan-2,5-dicarboxylate, bis(dibenzyl)furan-2,5-dicarboxylate, bis(dinonyl)furan-2,5-dicarboxylate, and bis(didecyl)furan-2,5-dicarboxylate, mixed alcohol derivatives, and mixtures of furan dicarboxylic acid esters and other plasticizers in varying ratios.

In an embodiment, the esterification process of the present invention can be carried out in a reaction zone comprising a pressure vessel while maintaining the alcohol:furan diacid mole ratio of from about 10:1.0 to about 0.8:1.0; from about 5.0:1.0 to about 1.0:1.0; or from about 3.0:1.0 to about 2.0:1.

The pressure within the reaction zone can be maintained from about 150 psig to about 15 psig (atmospheric pressure); from about 75 psig to about 15 psig; or from about 30 psig to about 15 psig. Alternatively, the pressure in the reaction zone can be maintained at below 150 psig, below 125 psig, below 100 psig, below 75 psig, below 50 psig, or below 25 psig. According to another embodiment, the pressure in the reaction zone can be maintained at above 10 psig, above 15 psig, above 25 psig, above 50 psig, above 75 psig, above 100 psig, or above 125 psig.

The temperature within the reaction zone can be maintained from about 300° C. to about 20° C. (room temperature); from about 250° C. to about 100° C.; or from about 200° C. to about 150° C. Alternatively, the temperature in the reaction zone can be maintained at below 300° C., below 250° C., below 200° C., or below 150° C. According to another embodiment, the temperature in the reaction zone can be maintained at above 20° C., above 50° C., above 75° C., above 100° C., above 125° C., above 150° C., above 175° C., above 200° C., above 250° C., or above 275° C.

The catalyst may be a compound soluble in the reaction mixture, i.e., soluble in the alcohol and the furan diester product. For example, the catalyst can be dibutyltin diacetate, dibutyltin oxide, titanium tetraisopropoxide, zirconium derivatives, iron derivatives, sulfuric acid, methanesulfonic acid, hydrochloric acid or mixtures thereof.

EXAMPLES

The process according to the embodiments described above is further illustrated by, but not limited to, the following examples wherein all percentages given are by weight unless specified otherwise.

Hydrogenation of Crude FDCA Procedure

A one liter autoclave equipped with a catalyst basket was charged with 67.5 g of crude colored FDCA that contained 4000 ppm of FFCA and 600.0 g of water. The catalyst basket was charged with 4.5 g of a palladium/carbon catalyst containing 0.5 wt. % palladium (CBA-300 SE 11233). The autoclave was sealed and heated to 170° C. while agitating the mixture. Hydrogen gas was introduced to attain 200 psig total pressure. The total pressure was maintained from a surge tank of hydrogen gas during the reaction. The reaction continued for 4 hours and gas supply was stopped and the autoclave was cooled to room temperature and depressurized. The heterogeneous mixture was filtered to isolate the purified FDCA. The mass of the filtrate was recorded. The purified FDCA solid was washed with 100 mL of water three times and it was oven dried at 110° C. under vacuum overnight and then weighed. The solid was analyzed by Gas Chromatography using BSTFA derivatization method, HPLC method and solution CIE color measurement method. Analytical results for the solid: >99.95% purity, <10 ppm FFCA, tetrahydrofuran dicarboxylic acid (THFDCA)=23 ppm and b*=0.25.

BEHFD Synthesis Using Purified FDCA

Purified FDCA (see above) was converted to BEHFD plasticizer via the following reaction. A 500 mL round bottom flask was fitted with an agitator and inlet port to supply a nitrogen atmosphere. The outlet port had a Dean-Stark trap and condenser to capture water and 2-EH alcohol as it was removed from the reactor. To the reactor was added 100 g purified FDCA and 208 g 2-ethylhexanol along with 1.47 g dibutyltin diacetate as catalyst. The reaction mixture was heated to 165° C. and the water removal monitored until it stopped coming over or the theoretical amount was captured in the Dean-Stark trap. The reaction was processed by removing the excess 2-ethylhexanol using vacuum (20-25 mm Hg) to a pot temperature of 165° C. The reaction mixture was filtered to remove any insolubles. 100 mL 5% NaOH water solution was added along with 100-200 mL toluene to aid layer separation at 50-55° C. The lower aqueous layer was decanted and the organic layer was washed two more times with 100 mL 5% NaHCO3 water solution. The reaction mixture was filtered through Celite and the cake rinsed with toluene. The toluene solution was stripped to a pot temperature of 130° C. with a vacuum of 160-165 mm Hg. A weight yield of 69-82% BEHFD was obtained (on larger batches with less sampling and handling losses the yield should be higher).

Analytical:
GC Analysis—98.99% Di-(2-ethylhexyl)furandicarboxylate Platinum-Cobalt Scale (Pt/Co scale or Apha-Hazen Scale): 30-40 APHA Color (visual comparison).

Yield: 82%

BEHFD Synthesis Using Crude FDCA

Crude FDCA that contains 4000 ppm of FFCA was converted to BEHFD plasticizer via the following reaction. A 500 mL round bottom flask was fitted with an agitator and inlet port to supply a nitrogen atmosphere. The outlet port had a Dean-Stark trap and condenser to capture water and 2-EH alcohol as it was removed from the reactor. To the reactor was added 100 g commercial FDCA and 208 g 2-ethylhexanol along with 1.47 g dibutyltin diacetate as catalyst. The reaction mixture was heated to 165° C. and the water removal monitored until it stopped coming over or the theoretical amount was captured in the Dean-Stark trap. The reaction was processed by removing the excess 2-EH using vacuum (20-25 mm Hg) to a pot temperature of 165° C. The reaction mixture was filtered to remove any insolubles. Added 100 mL 5% NaOH water solution along with 100-200 mL toluene to aid layer separation at 50-55° C. The lower aqueous layer was decanted and the organic layer was washed two more times with the last wash being 100 mL 5% NaHCO3 water solution. The reaction mixture was filtered through Celite and the cake rinsed with toluene. The toluene solution was stripped to a pot temperature of 130° C. with a vacuum of 160-175 mm Hg. A weight yield of 69-82% BEHFD was obtained (on larger batches with less sampling and handling losses the yield should be higher).

Analytical: GC Analysis—99% Di-(2-ethylhexyl)furandicarboxylate Platinum-Cobalt Scale (Pt/Co scale or Apha-Hazen Scale): 300-350 APHA Color (visual comparison).

Yield: 69%

Analytical

Gas Chromatographic Method for FDCA Solid Analysis:

Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

Gas Chromatographic Method for Detecting THFDCA (ppm Method):

Process samples were analyzed using a Shimadzu gas chromatograph Model 2010 (or equivalent) equipped with a split/splitless, heated injector (300° C.) and a flame ionization detector (300° C.). A capillary column (60 meter×0.32 mm ID) coated with a proprietary stationary phase (ZB-Multi-Residue-1) at 0.5 μm film thickness was employed. Helium was used as the carrier gas with an initial column head pressure of 11.5 psi and an initial column flow of 1.24 mL/minute while the carrier gas linear velocity of 19.7 cm/second was maintained constant throughout the entire oven temperature program. The column temperature was programmed as follows: The initial oven temperature was set at 50° C. and was held for 5 minutes, the oven was ramped up to 280° C. at 10° C./minute and was held at 280° C. for 32 minute (the total run time was 60 mins). 1.0-μl of the prepared sample solution was injected splitless. EZ-Chrom Elite chromatography data system software was used for data acquisition and data processing. The sample preparation was done by weighing 0.0280-0.0300 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 45 minutes to ensure complete derivitization. 1.0-μl of this prepared sample solution was injected for GC analysis.

Liquid Chromatographic Method for Low Level Measurement of FFCA in FDCA:

Samples were analyzed with an Agilent 1200 LC unit consisting of a quaternary pump, an auto sampler (3 uL injection), a thermostated column compartment (35C) and a diode array UV/vis detector (280 nm). The chromatograph was fitted with a 150 mm×4.6 mm Thermo Aquasil C18 column packed with 5 micron particles. The solvent flow program is shown in the table below: Channel A was 0.1% phosphoric acid in water, channel B was acetonitrile, and channel C was tetrahydrofuran (THF)

| Time (min) | % A | % B | % C | Flow (ml/min) |
|---|---|---|---|---|
| Initial | 95.0 | 0.0 | 5.0 | 1.50 |
| 7 | 95.0 | 0.0 | 5.0 | 1.50 |
| 10 | 15.0 | 80.0 | 5.0 | 1.50 |
| 12 | 15.0 | 80.0 | 5.0 | 1.50 |
| 12.1 | 95.0 | 0.0 | 5.0 | 1.50 |
| 15 | 95.0 | 0.0 | 5.0 | 1.50 |

Equilibration time: 1 minute

EZChrom elite is used for control of the HPLC and for data processing. A 5 point linear calibration was used in the (approximate) range of 0.25 to 100 ppm FFCA. Samples were prepared by dissolving ~0.05 g (weighed accurately to 0.0001 g) in 10 ml of 50:50 DMF/THF; higher sample weights may be used for samples where the FFCA is present at a very low level, provided that the solubility of FDCA is not exceeded. Sonication was used to ensure complete dissolution of the sample in the solvent. A portion of the prepared sample was transferred to an auto sampler vial for injection onto the LC.

Sample Preparation for b* Measurement:

Since hydrogenated FDCA was made in an autoclave without fixing the Pd/C catalyst in a bed, and some the carbon particulates became encapsulated within the FDCA solids, to obtain the true b* of the FDCA composition, some of the carbon particulates were first separated. A 10 wt % NH$_4$OH stock solution was prepared by diluting commercial 30 wt %

NH$_4$OH with water. 5.0 g of a dry FDCA solid was dissolved in 45.0 g of 10 wt % NH$_4$OH solution. The mixture was filtered using GHP Acrodisc 25 mm Syringe Filter to remove catalyst carbon particles. The b* of the solution was measured as discussed below:

Method for Measurement of b*:

Samples were analyzed using a Hunter Lab UltraScan Pro spectrophotometer with a diffuse illumination integrating light sphere. Per manufacturer recommendation the spectrophotometer was set to the CIELAB color scale with the D65 illuminate and 10° observer. The samples (in this case a 10 wt % NH$_4$OH stock solution but can also be) were transferred to a clear, disposable transmission cells having a 20 mm path length. The spectrophotometer was standardized in total transmission mode with a transmission cell filled with 10 wt % NH$_4$OH stock solution. The purpose of this standardization was to subtract the background color response of the cell and stock solution from the FDCA sample. The transmission of each sample was then measured to obtain the CIELAB value for b* using a Hunterlab EasyQuest QC software, version 4.30.

The Platinum-Cobalt Scale (Pt/Co Scale or Apha-Hazen Scale):

the Platinum-Cobalt Scale (Pt/Co scale or Apha-Hazen Scale) is also used to visually determine color of the sample by comparison. Color analysis on the final material was conducted using the visual comparison color method and the standard APHA color scale samples.

Interpretation of Results

Purification of Crude FDCA Via Hydrogenation:

During the oxidation of 5-HMF or its derivatives to FDCA a number of impurities are produced particularly mono-carboxylic acid species like 5-formyl furan-2-carboxyic acid (FFCA). These mono-carboxylic acids are less desirable since they terminate the chain of a polyester produced from a crude dicarboxylic acid. The crude dicarboxylic acid is purified by catalytic hydrogenation of the impurities in the following reactions:

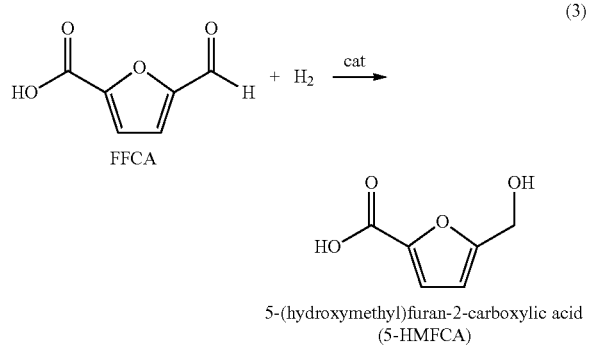

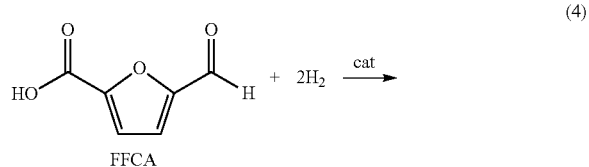

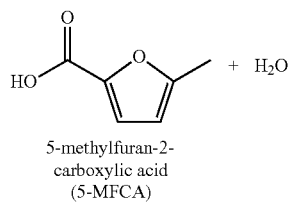

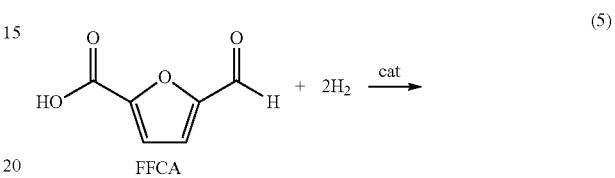

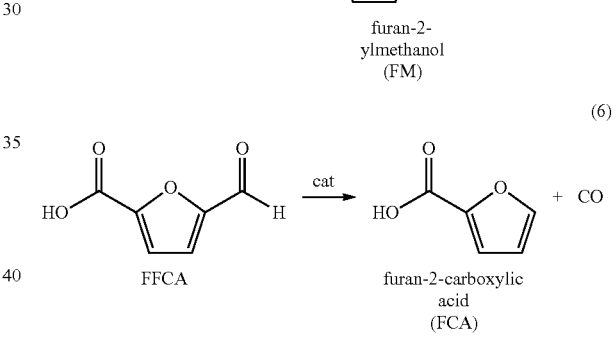

As can be seen above FFCA is converted to 5-HMFCA, 5-MFCA, FCA and FM which are water soluble. In addition colored bodies are reduced to water soluble products. The purification is generally carried out by dissolving the oxidation products in water at an elevated temperature and pressure followed by contacting the resulting solution with a bed of hydrogenation catalysts in the presence of hydrogen. The product mixture is allowed to cool which causes the purified product to crystallize whereas 5-HMFCA, 5-MFCA, FCA, FM and other hydrogenated impurities remain in solution.

Low Colored BEHFD Synthesis:

Esterification of crude FDCA that contains 4000 ppm of FFCA with 2-EH in presence of dibutyltin Diacetate catalyst produced a highly colored BEHFD with APHA color of 300-350 and purity of 98.99. Whereas esterification of purified FDCA with 2-EH in presence of dibutyltin Diacetate catalyst produced BEHFD with APHA color of only 30-40 and purity of 98.99%. These comparative examples demonstrate the improved color of the BEHFD if purified FDCA is used instead of crude FDCA.

In the low color BEHFD sample the following components were also identified by GC/MS:

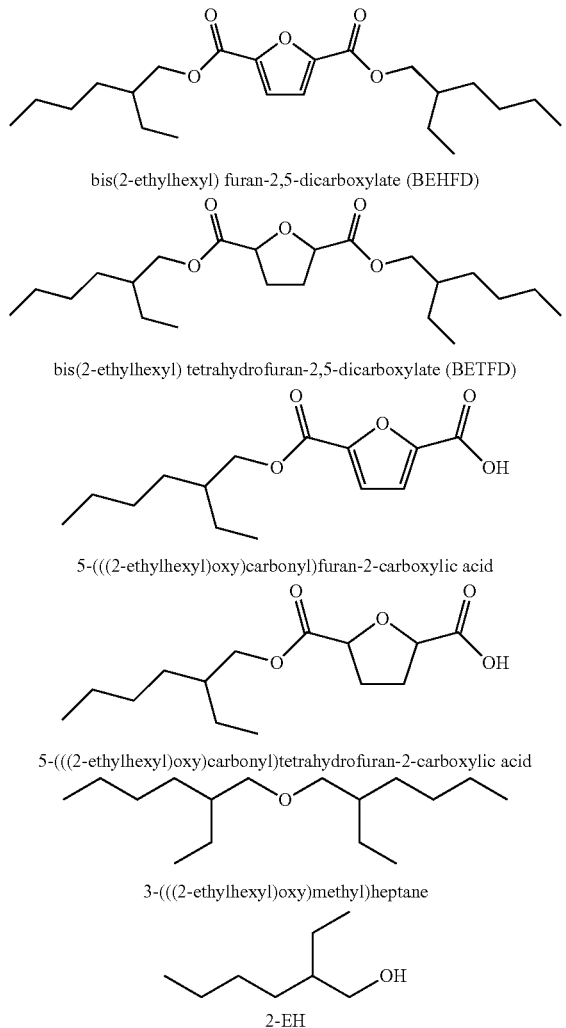

Although embodiments have been described in language specific to methodological acts, the embodiments are not necessarily limited to the specific acts described. Rather, the specific acts are disclosed as illustrative forms of implementing the embodiments.

What is claimed is:

1. A method for preparing a furan-2,5-dicarboxylate derivative plasticizer, comprising
contacting a purified furan-2,5-dicarboxylic acid composition and an alcohol stream comprising $C_4$-$C_{13}$ alcohols in the presence of a catalyst to produce a low color furan-2,5-dicarboxylate derivative plasticizer.

2. The method according to claim 1, wherein the furan-2,5-dicarboxylate derivative plasticizer has an APHA of less than 100.

3. The method according to claim 1, wherein the furan-2,5-dicarboxylate derivative plasticizer has a b* value of less than 10.

4. The method according to claim 1, wherein the alcohol stream comprises butanol, pentanol, hexanol, cyclohexanol, heptanol, 2-ethylhexanol (EH), cyclohexanemethanol, isomers of methylcyclohexanemethanol, octanol, nonanol, benzyl alcohol, 2-phenyl ethanol, decanol or mixtures thereof.

5. The method according to claim 1, wherein the purified furan-2,5-dicarboxylic acid composition has 5-formyl furan-2-carboxyic acid level of less than about 200 ppm.

6. The method according to claim 1, wherein the furan-2,5-dicarboxylate derivative plasticizer comprises dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl)furan-2,5-dicarboxylate, bis(dioctyl)furan-2,5-dicarboxylate, bis(dibenzyl)furan-2,5-dicarboxylate, bis(dinonyl)furan-2,5-dicarboxylate, bis(didecyl) furan-2,5-dicarboxylate or mixtures thereof.

7. A method for preparing a furan-2,5-dicarboxylate derivative plasticizer, comprising:
a) providing a crude furan 2,5-dicarboxylic acid composition comprising furan 2,5-dicarboxylic acid solids, 5-formyl furan-2-carboxyic acid, and a oxidation solvent composition;
b) combining a hydrogenation solvent composition with the furan 2,5-dicarboxylic acid solids and dissolving at least a portion of the furan 2,5-dicarboxylic acid solids to thereby produce a solvated furan 2,5-dicarboxylic acid composition comprising dissolved furan 2,5-dicarboxylic acid, the hydrogenation solvent composition, and 5-formyl furan-2-carboxyic acid;
c) in a hydrogenation reaction zone, hydrogenating the solvated furan 2,5-dicarboxylic acid composition at a temperature within a range of 130° C. to 225° C. by contacting the solvated furan 2,5-dicarboxylic acid composition with hydrogen in the presence of a hydrogenation catalyst to thereby hydrogenate 5-formyl furan-2-carboxyic acid and produce a hydrogenated furan 2,5-dicarboxylic acid composition comprising a hydrogenated 5-formyl furan-2-carboxyic acid species, dissolved furan 2,5-dicarboxylic acid, and the hydrogenation solvent; and
d) separating at least a portion of the dissolved FDCA from the hydrogenated furan 2,5-dicarboxylic acid composition to obtain a purified furan 2,5-dicarboxylic acid composition; and
e) contacting said purified furan 2,5-dicarboxylic acid composition and an alcohol stream in the presence of a catalyst to produce a low color furan-2,5-dicarboxylate derivative plasticizer.

8. The method according to claim 7, wherein the furan-2,5-dicarboxylate derivative plasticizer has an APHA of less than 100.

9. The method according to claim 7, wherein the furan-2,5-dicarboxylate derivative plasticizer has a b* value of less than 10.

10. The method according to claim 7, wherein the alcohol stream includes at least one of a $C_4$ to $C_{13}$ alcohol.

11. The method according to claim 10, wherein the alcohol stream comprises butanol, pentanol, hexanol, cyclohexanol, heptanol, 2-ethylhexanol (EH), cyclohexanemethanol, isomers of methylcyclohexanemethanol, octanol, nonanol, benzyl alcohol, 2-phenyl ethanol, decanol or mixtures thereof.

12. The method according to claim 7, wherein the purified furan-2,5-dicarboxylic acid composition has 5-formyl furan-2-carboxyic acid level of less than about 200 ppm.

13. The method according to claim 7, wherein the furan-2,5-dicarboxylate derivative plasticizer comprises dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl)furan-2,5-dicarboxylate, bis(dioctyl)furan-2,5-dicarboxylate, bis(dibenzyl)furan-2,5-dicarboxylate, bis(dinonyl)furan-2,5-dicarboxylate, bis(didecyl)furan-2,5-dicarboxylate or mixtures thereof.

14. A method for preparing a furan-2,5-dicarboxylate derivative plasticizer, comprising:
   a) oxidizing in an primary oxidation zone a composition including 5-(hydroxymethyl)furfural; 5-(hydroxymethyl)furfural esters; 5-(hydroxymethyl)furfural ethers; 5-alkyl furfurals; mixed feedstocks of 5-(hydroxymethyl)furfural and 5-(hydroxymethyl)furfural esters; mixed feedstocks of 5-(hydroxymethyl)furfural and 5-(hydroxymethyl)furfural ethers; mixed feedstocks of 5-(hydroxymethyl)furfural and 5-alkyl furfurals; or mixtures thereof in the presence of a solvent stream, an oxidizing gas stream, and a catalyst system to produce a carboxylic acid composition comprising 2,5-dicarboxylic acids;
   b) routing the carboxylic acid composition to a liquid displacement zone to produce a displaced mother liquid stream and a low impurity slurry stream; and
   c) routing the low impurity slurry stream to a secondary oxidation zone to form a purified slurry stream, wherein the purified slurry stream comprises purified 2,5-dicarboxylic acid composition and wherein the oxidizing temperature in the secondary oxidation zone is at least 10° C. higher that the oxidizing temperature in the primary oxidation zone; and
   d) contacting said purified 2,5-dicarboxylic acid composition and an alcohol stream in the presence of a catalyst to produce a low color furan-2,5-dicarboxylate derivative plasticizer.

15. The method according to claim 14, wherein the furan-2,5-dicarboxylate derivative plasticizer has an APHA of less than 100.

16. The method according to claim 14, wherein the furan-2,5-dicarboxylate derivative plasticizer has a b* value of less than 10.

17. The method according to claim 14, wherein the alcohol stream includes at least one of a $C_4$ to $C_{13}$ alcohol.

18. The method according to claim 17, wherein the alcohol stream comprises butanol, pentanol, hexanol, cyclohexanol, heptanol, 2-ethylhexanol (EH), cyclohexanemethanol, isomers of methylcyclohexanemethanol, octanol, nonanol, benzyl alcohol, 2-phenyl ethanol, decanol or mixtures thereof.

19. The method according to claim 14, wherein the purified furan-2,5-dicarboxylic acid composition has 5-formyl furan-2-carboxyic acid level of less than about 200 ppm.

20. The method according to claim 14, wherein the furan-2,5-dicarboxylate derivative plasticizer comprises dibutyl furan-2,5-dicarboxylate, dipentyl furan-2,5-dicarboxylate, dihexyl furan-2,5-dicarboxylate, diheptyl furan-2,5-dicarboxylate, bis(2-ethylhexyl)furan-2,5-dicarboxylate, bis(dioctyl)furan-2,5-dicarboxylate, bis(dibenzyl)furan-2,5-dicarboxylate, bis(dinonyl)furan-2,5-dicarboxylate, bis(didecyl)furan-2,5-dicarboxylate or mixtures thereof.

* * * * *